United States Patent [19]

Kobayashi et al.

[11] 4,326,024
[45] Apr. 20, 1982

[54] SILVER HALIDE EMULSION CONTAINING YELLOW-DYE-FORMING COUPLER

[75] Inventors: Hidetoshi Kobayashi; Mitsugu Tanaka, both of Minami-ashigara, Japan

[73] Assignee: Fuji Photo Film Co., Ltd., Kanagawa, Japan

[21] Appl. No.: 245,842

[22] Filed: Mar. 20, 1981

Related U.S. Application Data

[63] Continuation-in-part of Ser. No. 155,818, Jun. 2, 1980, abandoned.

[30] Foreign Application Priority Data

| May 31, 1979 [JP] | Japan | 54-68180 |
| May 28, 1980 [FR] | France | 80 11785 |
| May 29, 1980 [DE] | Fed. Rep. of Germany | 3020416 |
| Jun. 2, 1980 [GB] | United Kingdom | 1008/80 |

[51] Int. Cl.$^3$ ................................ G03C 1/40
[52] U.S. Cl. ................................ 430/557; 430/558
[58] Field of Search ............. 430/557, 558, 389, 472, 430/475

[56] References Cited

U.S. PATENT DOCUMENTS 4,046,575 9/1977 Boie et al. .............. 430/557
4,049,458 9/1977 Boie et al. .............. 430/557
4,182,630 1/1980 Quaglia .............. 430/558

*Primary Examiner*—J. Travis Brown
*Attorney, Agent, or Firm*—Sughrue, Mion, Zinn, Macpeak and Seas

[57] ABSTRACT

A silver halide color photosensitive material containing a yellow-dye-forming coupler having the formula (I):

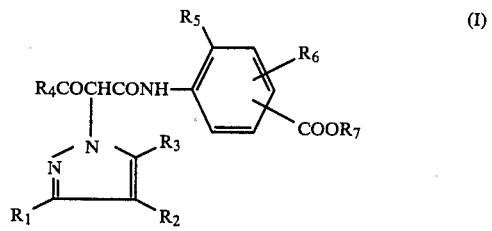

wherein $R_1$, $R_2$ and $R_3$ each independently represents a hydrogen, a halogen, an alkyl group, an alkoxy group, an aryloxy group, an alkoxycarbonyl group, an aryl group, a heterocyclic group or a carboxyl group; $R_4$ represents an aryl group or a tertiary alkyl group; $R_5$ and $R_6$ each independently represents a hydrogen, a halogen or an alkoxy group; and $R_7$ represents a substituted or unsubstituted alkyl group.

12 Claims, No Drawings

SILVER HALIDE EMULSION CONTAINING YELLOW-DYE-FORMING COUPLER

CROSS REFERENCE TO RELATED APPLICATION

This application is a continuation-in-part of U.S. application Ser. No. 155,818, filed June 2, 1980, now abandoned.

BACKGROUND OF THE INVENTION

1. Field of the Invention

The present invention relates to a two-equivalent yellow coupler having improved color developing properties, color photographic photosensitive materials containing said coupler, and an image-forming method using this type of coupler.

2. Description of the Prior Art

In color photosensitive materials, it is highly desired to form a color image showing a high sensitivity, a high gamma value and a high contrast, and a fundamental way of achieving this is to select an appropriate group for elimination (i.e., coupling-off group) when using a two-equivalent coupler. Of course, the other properties of the coupler should not be sacrificed in the accomplishment of this purpose. Examples of such coupling-off groups are aryloxy groups as disclosed in U.S. Pat. No. 3,408,194, acyloxy groups as described in U.S. Pat. No. 3,447,928, imido groups as described in Japanese Patent Application (OPI) Nos. 26133/72 (the term "OPI" as used herein refers to a "published unexamined Japanese patent application") and 13576/74, triazolyl groups as described in Japanese Patent Application (OPI) No. 17438/76, tetrazolyl groups as described in Japanese patent application (OPI) No. 145319/76, aminosulfonyloxy groups as described in Japanese Patent Publication No. 12661/74, sulfinyloxy groups as described in Japanese patent publication No. 12660/74, benzotriazolyl groups as described in British Pat. Nos. 1,450,479 and 1,476,760, and pyrazolyl groups as described in U.S. Pat. No. 4,049,458.

But U.S. Pat. No. 4,049,458 does not disclose an aryl group substituted with an alkoxycarbonyl group for $R_4$ in a formula (I) thereof.

Further, most of these coupling-off groups are not entirely satisfactory, due to various disadvantages, such as inadequate reactivity in the coupling reaction, poor dispersibility (which causes difficulties in coating), color fogging, difficulties in coupler synthesis, poor stability of the color image formed, and poor shelf life of the coupler.

SUMMARY OF THE INVENTION

The object of the present invention is to provide a novel two-equivalent yellow coupler which has excellent color developing properties (high sensitivity, high gamma value and high contrast). Needless to say, the other properties of the coupler should not be sacrificed in order to accomplish this purpose.

This and other objects of the invention that will be readily apparent from the following disclosure can be accomplished by means of a yellow-dye-forming coupler of the formula (I):

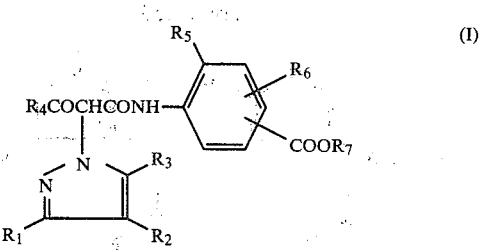

wherein $R_1$, $R_2$ and $R_3$ each independently (that is, although selected from the same group of possible substituents, the individual substituents are independently selected and are not necessarily identical) represents hydrogen, a halogen, an alkyl group having 1 to 24 carbon atoms (e.g., methyl, octyl, hexadecyl, benzyl, carboxymethyl, t-butyl, isopropyl, eicosyl, trifluoromethyl, phenoxymethyl, etc.), an alkoxy group having 1 to 24 carbon atoms (e.g., methoxy, octyloxy, hexadecyloxy, benzyloxy, 2-methoxyethoxy, etc.), an aryloxy group having 6 to 24 carbon atoms (e.g., phenoxy, 4-methylphenoxy, 2-methoxyphenoxy, etc.), an alkoxycarbonyl group having 2 to 24 carbon atoms (e.g., methoxycarbonyl, hexadecyloxycarbonyl, etc.), an aryl group having 6 to 24 carbon atoms (e.g., phenyl, 4-methylphenyl, 4-methoxyphenyl, 3-chlorophenyl, etc.), a heterocyclic group having 2 to 24 carbon atoms (e.g., oxazolyl, thiazolyl, furyl, α-pyridyl, etc.) or a carboxyl group; $R_4$ represents an aryl group, including an aryl group substituted with an alkyl group having 1 to 6 carbon atoms, an acylamino group having 2 to 30 carbon atoms or an alkoxy group having 1 to 24 carbon atoms, or a tertiary alkyl group having 4 to 30 carbon atoms; $R_5$ and $R_6$ each independently represents hydrogen, halogen, or an alkoxy group having 1 to 24 carbon atoms; and $R_7$ represents a straight or branched chain alkyl group having 1 to 24 carbon atoms, including an alkyl group substituted with, for example, an alkoxy group, a phenoxy group, an alkoxycarbonyl group, an alkylthio group or a halogen atom.

DETAILED DESCRIPTION OF THE INVENTION

Preferred examples of the coupling-off group in the compound of the formula (I) are as follows:

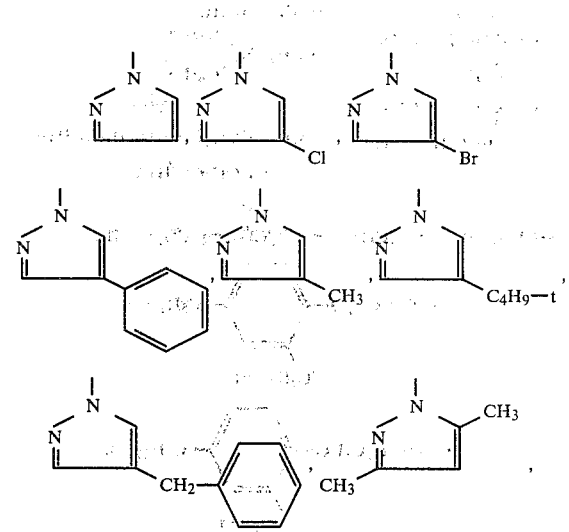

-continued

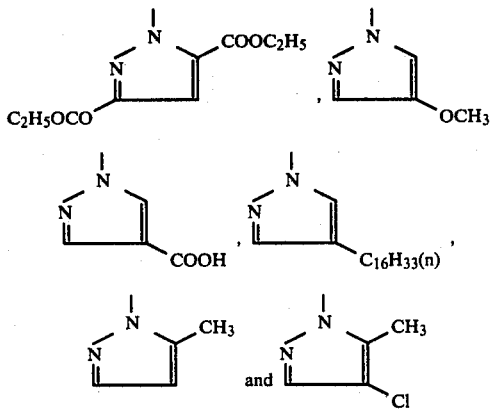

Preferred examples of R₄ are as follows:

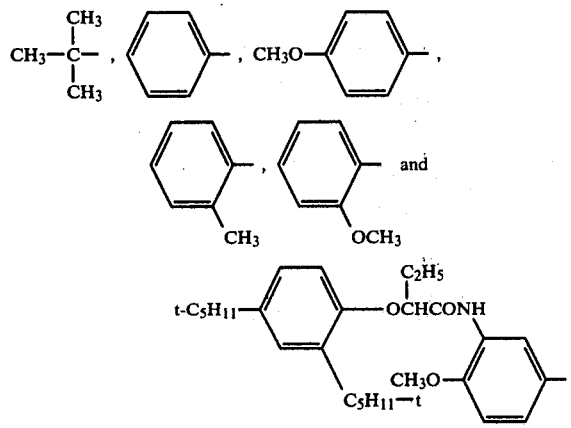

$R_5$ is preferably selected from the group consisting of hydrogen, chlorine, methoxy and tetradecyloxy group.

In preferred anilino group substituted with $R_5$, $R_6$ and —COOR$_7$, $R_5$ represents chlorine atom or a methoxy group; $R_6$ represents a hydrogen atom.

Specific examples of R₇ are as follows:

—(CH₂)₅CH₃,        —(CH₂)₁₁CH₃,
—(CH₂)₁₃CH₃,       —(CH₂)₁₅CH₃,
—CH₂CH(CH₂)₃CH₃,   —CH₂CH<C₈H₁₇/C₆H₁₃,
       |
       C₂H₅
—CH₂CH(CH₂)₇CH₃,            CH₃
       |                     |
       CH₂(CH₂)₅CH₃   —CH₂CHCH₂CH₂CHCH₂C(CH₃)₃
                             |
                             CHCH₂C(CH₃)₃
                             |
                             CH₃
—CH₂CH₂O(CH₂)₁₁CH₃,  ─(CH₂CH₂O)₂(CH₂)₁₁CH₃,

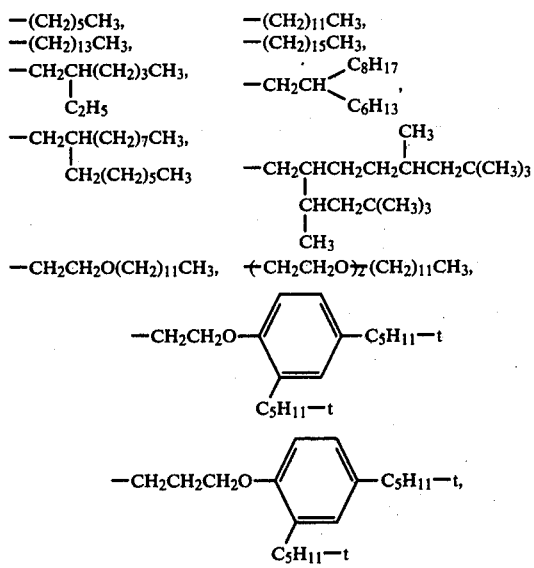

-continued
—CH₂COO(CH₂)₁₁CH₃,

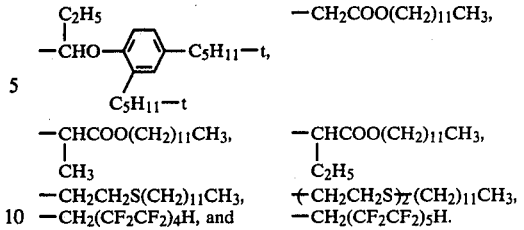

—CHCOO(CH₂)₁₁CH₃,    —CHCOO(CH₂)₁₁CH₃,
 |                    |
 CH₃                  C₂H₅
—CH₂CH₂S(CH₂)₁₁CH₃,  ─(CH₂CH₂S)₂(CH₂)₁₁CH₃,
—CH₂(CF₂CF₂)₄H, and  —CH₂(CF₂CF₂)₅H.

Couplers similar to the yellow coupler of the formula (I) are disclosed in British Pat. Nos. 1,450,479 and 1,476,760.

Examples of yellow couplers disclosed in British Pat. No. 1,450,479 may have the coupling-off groups

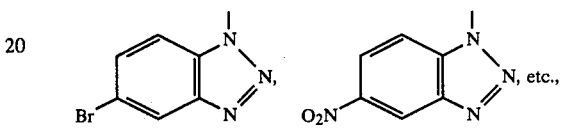

and examples of couplers in British Pat. No. 1,476,760 may have the following coupling-off groups

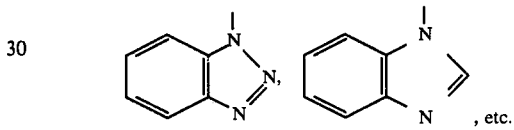

However, many of the couplers disclosed in these British Patents still have undesirable defects, for example, the sensitivity may be deteriorated caused by the coupler per se or by the interaction between silver halide and a heterocyclic compound produced by a coupling reaction (for example, by adsorption to the photosensitive grains), there is a tendency to low gamma values and low optical density, and the like.

The coupler in accordance with this invention is free from such defects as are described above with respect to the basic characteristics required of a photographic photosensitive material, and hence render a truly improved coupler.

Couplers similar to the yellow coupler of this invention are disclosed in U.S. Pat. No. 4,049,458. However, the couplers disclosed in U.S. Pat. No. 4,049,458 have remarkably lower optical density than that of the couplers of this invention.

Thus, a primary feature of the couplers in accordance with this invention is that they have excellent color developing properties and exhibit excellent color developing performance even in color developing processes carried out at a high pH.

A second feature of the couplers in accordance with this invention is that the synthesis thereof is trouble-free and the yield is high.

A third feature of couplers in accordance with this invention is that, when processed, a dye can be formed in a high yield without fogging or staining; the stain produced by red prussiate on bleaching is especially reduced.

A fourth feature of couplers in accordance with this invention is that the emulsifiability thereof is excellent, and a stable emulsion is thus produced.

Preferred examples of couplers in accordance with the invention according to formula (I) are as follows:
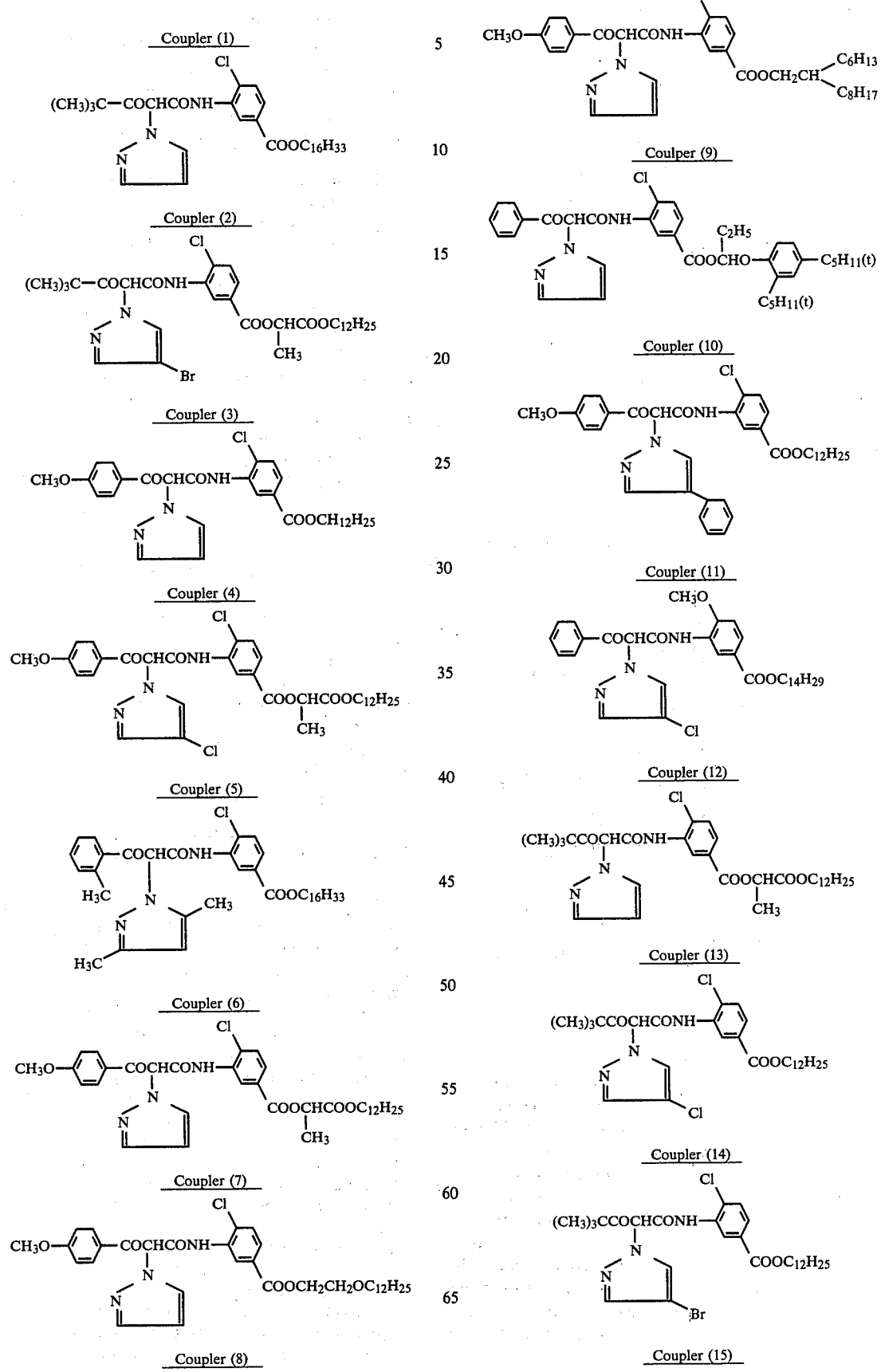

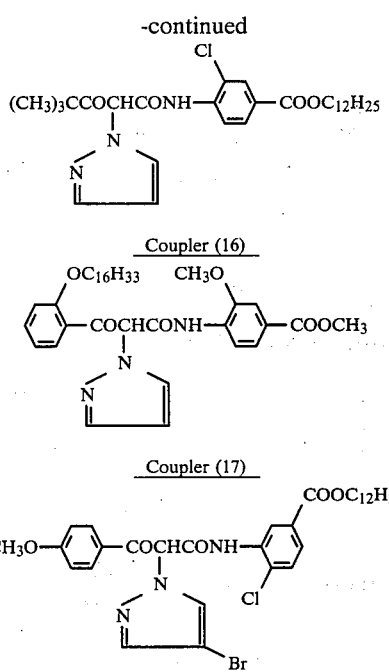

The couplers according to this invention can be synthesized from a four-equivalent coupler according to a reaction scheme as shown below:

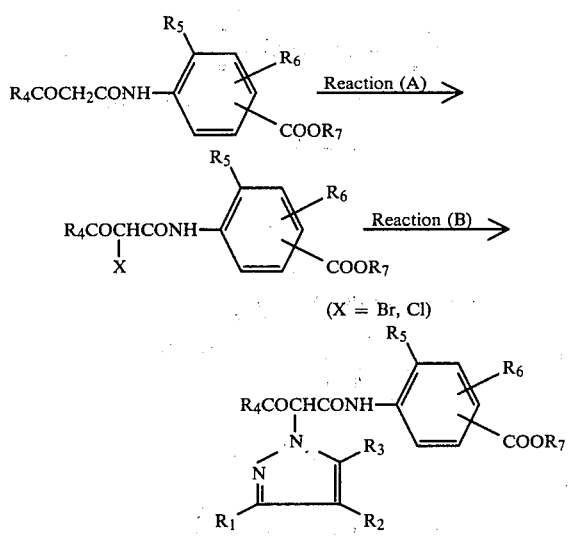

For Reaction (A), it is preferred to carry out the reaction in a halogen-containing solvent such as chloroform, dichloromethane, dichloroethane or the like, and the use of bromine, N-bromosuccinimide or the like for the bromination or sulfuryl chloride or the like for the chlorination gives the desired halogenated product at a high yield. In Reaction (B), the halogenated product and from 1 to 10-equivalents of pyrazole can be reacted without solvent or in an aprotic polar solvent such as dimethylformamide, hexamethylphosphoramide, dichloroethane, chloroform, sulfolane or the like to obtain the desired coupler at a high yield. In addition, a base such as triethylamine, potassium hydroxide or the like may be employed in Reaction (B).

PREPARATION EXAMPLE 1

Synthesis of α-(4-methoxybenzoyl)-α-pyrazolyl-2-chloro-5-dodecyloxycarbonylacetanilide, Coupler (3)

52 g of α-(4-methoxybenzoyl)-2-chloro-5-dodecyloxycarbonylacetanilide was dissolved in 500 ml of chloroform. 16 g of bromide was dropwisely added to the solution under ice-cool while stirring. Then, the reaction solution was washed with water to remove hydrogen bromide and the resulting chloroform solution was concentrated to obtain α-(4-methoxybenzoyl)-α-bromo-2-chloro-5-dodecyloxycarbonylacetanilide (i.e., brominated product). The brominated product and 14 g of pyrazole were reacted in 100 ml of dimethylformamide at 90° C. for 2 hours with stirring. 400 ml of ethyl acetate was added to the reaction mixture and washing with water was repeated several times. The ethyl acetate layer was dried on anhydrous sodium sulfate and then concentrated. The residue was crystallized from methanol to obtain Coupler (3), yield 52 g, m.p. 108°–109° C.

Elemental Analysis:

Calc'd (%): H: 6.93; C: 66.02; N: 7.22; Found (%): H: 6.78; C: 66.08; N: 7.23.

PREPARATION EXAMPLE 2

Synthesis of α-(4-methoxybenzoyl)-α-(4-bromopyrazolyl)-2-chloro-5-dodecyloxycarbonylacetanilide, Coupler (17)

The same treatment as Preparation Example 1 was carried out except for using 30 g of 4-bromopyrazole in place of pyrazole. The resulting product was crystallized from a mixed solvent of ethyl acetate and methanol to obtain Coupler (17), yield 56 g, m.p. 92°–94° C.

Elemental Analysis:

Calc'd (%): H: 5.95; C: 58.14; N: 6.36; Found (%): H: 6.00; C: 58.19; N: 6.43.

PREPARATION EXAMPLE 3

Synthesis of α-pivaloyl-α-pyrazolyl-2-chloro-5-hexadecyloxycarbonylacetanilide, Coupler (1)

47 g of α-pivaloyl-2-chloro-5-hexadecyloxycarbonylacetanilide was dissolved in 500 ml of chloroform. 16 g of bromide was dropwisely added to the solution under ice-cool while stirring. Then, the reaction solution was washed with water to remove hydrogen bromide and the resulting chloroform layer was concentrated to obtain α-pivaloyl-α-bromo-2-chloro-5-hexadecyloxycarbonylacetanilide (i.e., brominated product). The brominated product and 14 g of pyrazole were reacted at 90° C. for 2 hours with stirring. 400 ml of ethyl acetate was added to the reaction mixture and washing with water was repeated several times. The ethyl acetate layer was dried on anhydrous sodium sulfate and then concentrated. The residue was crystallized from methanol to obtain Coupler (1), yield 49 g, m.p. 65° C.

Elemental Analysis:

Calc'd (%): H: 7.96; C: 65.46; N: 7.90; Found (%): H: 7.92; C: 65.51; N: 7.86

In order to produce a silver halide color photographic photosensitive material in accordance with the invention, a coupler in accordance with the invention may be employed alone, or two or more of such couplers may be employed in a mixture.

It is possible to incorporate in the photographic photosensitive material containing the coupler or couplers in accordance with this invention, for example, DIR couplers and DIR compounds (such as those described in U.S. Pat. Nos. 3,632,345, 3,227,554 and 3,379,529, Japanese patent application (OPI) No. 135310/75, British Pat. Nos. 1,450,479 and 1,476,760), yellow-dye-forming couplers (such as those described in West German patent application (OLS) No. 2,213,461, U.S. Pat. Nos. 3,510,306, 3,644,498 and 3,894,875), magenta-dye-forming couplers (such as those described in U.S. Pat. No. 3,615,506, West German patent application (OLS) Nos. 2,418,959, 2,424,467, etc.) and cyan-dye-forming couplers (such as those described in U.S. Pat. Nos. 2,474,293, 3,034,892, 3,591,383, 3,311,476, 3,476,563, etc.) and the like.

Conveniently, the coupler in accordance with this invention can be dispersed in a photographic emulsion as a solution in an organic solvent. A mode of dispersing the coupler is illustrated in detail in U.S. Pat. No. 3,676,131. The organic solvent useful for dissolving the coupler should be sparingly soluble in water and have a high boiling point, such as substituted hydrocarbons, carboxylic acid esters, benzoic acid ester, citric acid ester, carboxylic acid amides, phosphoric acid esters, ethers and the like. Representative examples thereof include di-n-butyl phthalate, n-octyl benzoate, o-acetyltributyl citrate, tricresyl phosphate, tri-n-hexyl phosphate, and N,N-diethylcaprylamide. It is also advantageous to employ, in addition to the above-mentioned high boiling solvents, an auxiliary solvent having a low boiling point in order to facilitate the dissolution of the coupler. Representative examples thereof include propylene carbonate, ethyl acetate, butyl acetate, cyclohexanol, tetrahydrofuran, cyclohexane.

In order to facilitate the dispersion of the solvent in a hydrophilic colloid used in the photographic emulsion in a minutely dispersed form, it is advantageous to employ a surfactant.

The amount of the coupler used is generally from about 5 to 1,500 g per mol of silver halide, but the amount added can vary depending on the various application purposes, and preferably such amount is from 10 to 500 g per mol of silver halide.

The coupler may be applied to various silver halide photosensitive materials such as color negative films, color positive films, color reversal films, color paper (that is, photographic paper for forming a color print image) and various other color photosensitive materials, among which it is especially preferably applied to color reversal films and color paper.

A coupler in accordance with the invention may be applied in a multilayer construction method of a multi-layered color photosensitive material (such as those described in U.S. Pat. Nos. 3,726,681 and 3,516,831, British Pat. Nos. 818,687 and 923,045, etc.), in a method as described in Japanese patent application (OPI) No. 5179/75, in a method as described in West German patent application (OLS) No. 2,322,165, or in a method of using it in combination with DIR compounds as is described in U.S. Pat. No. 3,703,375.

The photosensitive material used in this invention may contain a p-substituted phenol derivative such as a hydroquinone derivative or the like in the emulsion layer or its adjacent layers. This is advantageous for stabilizing the color image. Especially effective p-substituted phenol derivatives are those described in U.S. Pat. Nos. 2,360,290, 2,418,613, 2,675,314, 2,710,801, 2,728,659, 2,732,300, 2,735,765, 2,816,028, 3,457,079, 3,069,262, Japanese patent publication No. 13496/68, U.S. Pat. No. 2,735,765, Japanese patent application (OPI) No. 4738/72, U.S. Pat. Nos. 3,432,300, 3,573,050, 3,574,627 and 3,764,337.

The photosensitive material containing the coupler in accordance with this invention may contain an ultraviolet light absorbing agent in the emulsion layer or layers adjacent thereto for stabilizing the color images, examples of such agents being those described in U.S. Pat. Nos. 3,250,617, 3,253,921, etc.

A coupler in accordance with this invention may be employed even in a low-silver photographic material in which the amount of a silver halide in the emulsion layer is from one half to one-hundredth the amount employed in ordinary photographic materials. With such a color photosensitive material having a reduced content of a silver halide, an adequate color image can be obtained by a color image forming method involving increasing the amount of a dye formed utilizing color intensification, which employs a peroxide, a cobalt complex, sodium chlorite (described, for example, in West German patent application (OLS) No. 2,357,694, U.S. Pat. Nos. 3,674,490, 3,761,265, West German patent application (OLS) Nos. 2,044,833, 2,056,359, 2,056,360, 2,226,770, Japanese patent application (OPI) Nos. 9728/73, 9729/73, etc.), or the like.

In order to color develop a photosensitive material containing a coupler in accordance with the invention, conventional methods may be generally applied. More specifically, a dye image and a silver image are formed by the color development with a substituted p-phenylenediamine, the silver is subsequently oxidized in a bleaching bath, and the remaining silver halide and other silver salts are removed by dissolving in a fixing bath, thereby leaving only the dye image. A prehardener bath, a neutralizer bath, a first developing bath, an image stabilizing bath, etc., may also be employed in combination with the foregoing according to the necessity and desirability thereof.

Various known compounds may be employed as the p-phenylenediamine derivative for developing the color photosensitive material in accordance with the invention. Especially useful p-phenylenediamine type color developing agents are N,N-dialkyl-p-phenylenediamine type compounds, in which the alkyl and phenyl groups may be substituted. Among these, particularly useful compounds include, for example, N,N-diethyl-p-phenylenediamine hydrochloride, N-methyl-p-phenylenediamine hydrochloride, N,N-dimethyl-p-phenylenediamine hydrochloride, 2-amino-5- (N-ethyl-N-dodecylamino)toluene, N-ethyl-N-($\beta$-methanesulfonamidoethyl-3-methyl-4-aminoaniline sulfate, N-ethyl-N-$\beta$-hydroxyethylaminoaniline, 4-amino-N-(2-methoxyethyl)-N-ethyl-3-methylaniline-p-toluenesulfonate, N,N-diethyl-3-methyl-4-aminoaniline, and N-ethyl-N-($\beta$-hydroxyethyl)-3-methyl-4-aminoaniline.

Examples of useful bleaching agents include persulfates, bichromates, red prussiate (i.e., potassium ferricyanide), hydrogen peroxide, and ferric ion complex salts. The ferric ion complex salts are complexes of a ferric ion and a chelating agent, such as an amino polycarboxylic acid, an amino polyphosphonic acid, their salts, and so forth. The amino polycarboxylic acid salts or the amino polyphosphonic acid salts are salts of amino polycarboxylic acids or amino polyphosphonic acids with alkali metals, ammonium, water-soluble amines, etc. The ferric ion complex salt may be employed in the form of the complex salt, or may be produced by using ferric sulfate, ferric chloride, ammonium ferric nitrate, ferric phosphate or the like and a chelating agent such as an amino polycarboxylic acid or an amino polyphosphonic acid in solution. The photosensitive material containing the coupler in accordance with the invention is characterized by reduced stain formation even when processed in a bleaching bath containing a strong oxidizing agent such as a bichromate or red prussiate, thus giving a good color image.

Examples of fixing agents that can be used include thiosulfates (e.g., ammonium thiosulfate, sodium thiosulfate, potassium thiosulfate, etc.), thiocyanates (e.g., ammonium thiocyanate, sodium thiocyanate, potassium thiocyanate, etc.), and thioether compounds (e.g., 3,6-dithia-1,8-octanediol, etc.). These fixing agents may be employed alone or as mixtures thereof.

While coupler in accordance with this invention may be applied to any process using ordinary silver halide color photosensitive materials such as color negative films, color paper, color positive films, color reversal films for slides, color reversal films for motion pictures, color reversal films for television, etc., it is preferably applied especially to the color paper and color reversal films because it especially exhibits excellent color developing performance in processes using such materials.

The invention will be more particularly described in the following Examples.

EXAMPLE 1

100 g of Coupler (16) of this invention was dissolved in 100 ml of tricresyl phosphate and 100 ml of ethyl acetate, and mixed with rapid stirring with 1 kg of a 10% gelatin aqueous solution to obtain an emulsion. 350 g of the resulting emulsion was mixed with 1 kg of a blue-sensitive silver iodobromide emulsion (containing 50 g of silver and 60 g of gelatin, iodine content 6 mol%) to prepare Coating Solution A.

The Coating Solution A was coated on a cellulose triacetate film support provided with a subbing layer in a coated silver amount of 2.25 g/m² and thereon a 5% gelatin aqueous solution was coated at a dry thickness of 1μ to provide a protective layer. Thus, Sample A was obtained.

Instead of the above Coupler (16), 107 g of a yellow coupler (I) described in U.S. Pat. No. 4,049,458 was used and by the same procedures as Coating Solution A above, there was prepared Coating Solution B. The Coating Solution B was coated on a cellulose triacetate film support having a subbing layer in the same coated silver amount and the same coated coupler amount (the same mol) per unit area as those of Sample A and thereon a protective layer was provided in the same manner as Sample A to prepare Sample B.

Coupler (I): (disclosed in U.S. Pat. No. 4,049,458)

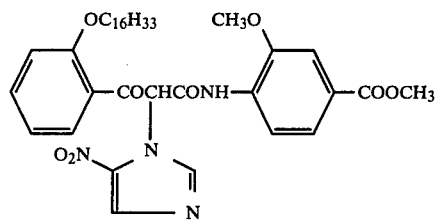

Each of these samples was exposed to light for sensitometry and subjected to the following process:

| Process | Temperature (°C.) | Time |
|---|---|---|
| 1. Color development | 38 | 3 min 15 sec |
| 2. Bleaching | " |  |
| 3. Washing with water | " | 3 min 15 sec |
| 4. Fixing | " | 6 min 30 sec |
| 5. Washing with water | " | 3 min 15 sec |
| 6. Stabilization | " | 3 min 15 sec |

The respective process solutions in the above process had the following compositions:

| Color Development Solution | |
|---|---|
| Sodium nitrotriacetate | 1.0 g |
| Sodium sulfite | 4.0 g |
| Sodium carbonate | 30.0 g |
| Potassium bromide | 1.4 g |
| Hydroxylamine sulfate | 2.4 g |
| 4-(N-Ethyl-N-β-hydroxyethylamino)-2-methyl-aniline sulfate | 4.5 g |
| Water to make | 1 l |
| Bleaching Solution | |
| Ammonium bromide | 160.0 g |
| Aqueous ammonia (28%) | 25.0 ml |
| Iron (III) ammonium ethylenediaminetetraacetate | 130.0 g |
| Glacial acetic acid | 14.0 ml |
| Water to make | 1 l |
| Fixing Solution | |
| Sodium tetrapolyphosphate | 2.0 g |
| Sodium sulfite | 4.0 g |
| Ammonium thiosulfate (70%) | 175.0 ml |
| Sodium bisulfite | 4.6 g |
| Water to make | 1 l |
| Stabilizing Solution | |
| Formalin (37% by weight) | 8.0 ml |
| Water to make | 1 l |

Each of the samples thus processed was measured for optical density using a blue light and the results are shown in Table 1 below.

TABLE 1

| Sample | Coupler | Fog | Gamma | Sensitivity | Density* |
|---|---|---|---|---|---|
| A | (16) (invention) | 0.06 | 2.4 | 0 | 2.32 |
| B | (I) (comparison) | 0.06 | 1.6 | −0.25 | 1.84 |

*density at a shoulder portion of density curve

From Table 1 above, it can be seen that the coupler in accordance with this invention has superior color formation as compared with the comparative Coupler (I) of U.S. Pat. No. 4,049,458.

EXAMPLE 2

According to the same procedures as Example 1, Coupler (3) of this invention and comparative Couplers (II), (III) and (IV) which are within the scope of U.S. Pat. No. 4,049,458, respectively, were coated in the same coated silver amount and the same coated coupler amount (the same mol number) per unit area, and thereon a protective layer was provided to prepare Samples C, D, E and F, respectively.

Comparative Coupler (II): (within the scope of U.S. Pat. No. 4,049,458)

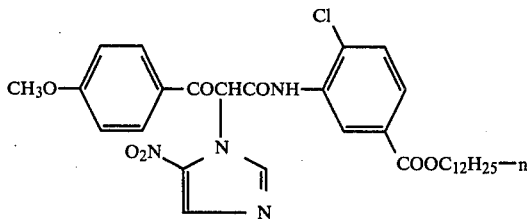

Comparative Coupler (III): (within the scope of U.S. Pat. No. 4,049,458)

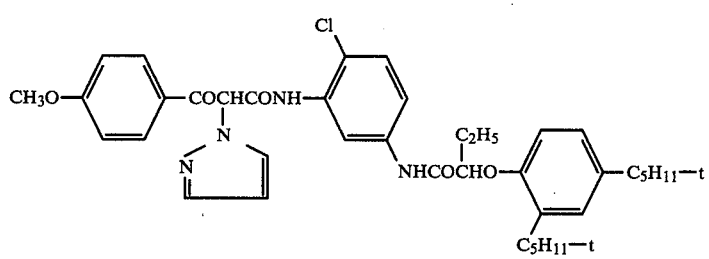

Comparative Coupler (IV): (within the scope of U.S. Pat. No. 4,049,458)

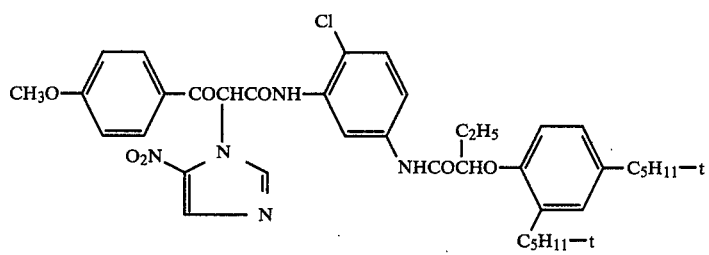

Each of these samples was exposed to light for sensitometry and subjected to the same process as Example 1. Each of the samples thus-processed was measured for optical density using a blue light and the results are shown in Table 2 below.

TABLE 2

| Sample | Couple | Fog | Gamma | Sensitivity | Density* |
|---|---|---|---|---|---|
| C | (3) (invention) | 0.05 | 2.8 | 0 | 2.68 |
| D | (II) (comparison) | 0.06 | 2.2 | −0.10 | 2.24 |
| E | (III) (comparison) | 0.05 | 1.8 | −0.24 | 1.98 |
| F | (IV) (comparison) | 0.05 | 1.6 | −0.26 | 1.91 |

*density at a shoulder portion of density curve

From Table 2 above, it can be seen that the coupler in accordance with this invention has superior color formation as compared with comparative couplers being within the scope of U.S. Pat. No. 4,049,458.

EXAMPLE 3

100 g of Coupler (3) of this invention was dissolved in 60 ml of tricresyl phosphate and 100 ml of ethyl acetate, and mixed with rapid stirring with 1 kg of a 10% gelatin aqueous solution to obtain an emulsion. 940 g of thus-obtained emulsion was mixed with 1 kg of a blue-sensitive silver iodobromide emulsion (containing 60 g of silver and 60 g of gelatin, iodide content 5 mol%) and coated at a dry thickness of 3.5μ on a cellulose triacetate film support provided with a subbing layer. A 5% gelatin aqueous solution was coated thereon at a dry thickness of 1μ to provide a protective layer. Thus, Sample G was obtained.

In the same manner as above, the comparative couplers (II), (III) and (IV), respectively, were coated in the same coated silver amount and the same coated coupler amount (mol number) per unit area and thereon a protective layer was provided to obtain Samples H, I and J, respectively.

These Samples G, H, I and J were exposed to light for sensitometry and subjected to the following color reversal process steps:

| Process | Temperature | Time |
|---|---|---|
| First development | 38° C. | 3 min |
| Washing with water | " | 1 min |
| Reversal | " | 2 min |
| Color development | " | 6 min |
| Compensation | " | 2 min |
| Bleaching | " | 6 min |
| Fixing | " | 4 min |
| Washing with water | " | 4 min |
| Stabilization | " | 1 min |
| Drying | | |

The process solutions of the respective process steps had the following compositions:

| First Development Step Solution | |
|---|---|
| Water | 800 ml |
| Sodium tetrapolyphosphate | 2.0 g |
| Sodium bisulfite | 8.0 g |
| Sodium sulfite | 37.0 g |
| 1-Phenyl-3-pyrazolidone | 0.35 g |
| Hydroquinone | 5.5 g |
| Sodium carbonate (monohydrate) | 28.0 g |
| Potassium bromide | 1.5 g |
| Potassium iodide | 13.0 mg |
| Sodium thiocyanate | 1.4 g |
| Water to make | 1.0 l |
| Reversal Step Solution | |
| Water | 800 ml |
| Nitrilo-N,N,N-trimethylphosphonic acid sexisodium salt | 3.0 g |
| Stannous chloride (dihydrate) | 1.0 g |

| -continued | |
| --- | --- |
| Sodium hydroxide | 8.0 g |
| Glacial acetic acid | 15.0 ml |
| Water to make | 1.0 l |
| Color Development Step Solution | |
| Water | 800 ml |
| Sodiom tetrapolyphosphate | 2.0 g |
| Benzyl alcohol | 5.0 ml |
| Sodium sulfite | 7.5 g |
| Sodium tertiary phosphate (dodecahydrate) | 36.0 g |
| Potassium bromide | 1.0 g |
| Potassium iodide | 90.0 mg |
| Sodium hydroxide | 3.0 g |
| Citrazinic acid | 1.5 g |
| 4-Amino-3-methyl-N-ethyl-β-hydroxy-ethylaniline sesquisulfate monohydrate | 11.0 g |
| Ethylenediamine | 3.0 g |
| Water to make | 1.0 l |
| Compensation Step Solution | |
| Water | 800 ml |
| Glacial acetic acid | 5.0 ml |
| Sodium hydroxide | 3.0 g |
| Dimethylaminoethaneisothiourea (dihydrochloride) | 1.0 g |
| Water to make | 1.0 l |
| Bleaching Step Solution | |
| Water | 800 ml |
| Sodium ethylenediaminetetraacetate (dihydrate) | 2.0 g |
| Ammonium ferric (III) ethylenediamine-tetraacetate (dihydrate) | 120.0 g |
| Potassium bromide | 100.0 g |
| Water to make | 1.0 l |
| Fixing Step Solution | |
| Water | 800 ml |
| Ammonium thiosulfate | 80.0 g |
| Sodium sulfite | 5.0 g |
| Sodium bisulfite | 5.0 g |
| Water to make | 1.0 l |
| Stabilization Step Solution | |
| Water | 800 ml |
| Formalin (37% by weight) | 5.0 ml |
| Fuji Driwel (trademark) | 5.0 ml |
| Water to make | 1.0 l |

Each of the samples thus-obtained was measured for optical density using a blue light filter.

The gamma values and the maximum densities of the respective yellow color images obtained from these samples are summarized in Table 3 below.

TABLE 3

| Sample | Coupler | Gamma | Maximum Density |
| --- | --- | --- | --- |
| G | (3) (invention) | 2.15 | 3.52 |
| H | (II) (comparison) | 1.74 | 2.88 |
| I | (III) (comparison) | 1.45 | 2.53 |
| J | (IV) (comparison) | 1.41 | 2.45 |

From Table 3 above, it can be seen that the coupler in accordance with the invention has a higher maximum density and gamma as compared with the comparative couplers.

EXAMPLE 4

Emulsion layers and auxiliary layers were applied in the following order to a cellulose triacetate base provided with the following layer.

First Layer: Red-Sensitive Emulsion Layer 100 g of a cyan coupler, 1-hydroxy-2-[γ-(2,4-di-t-amylphenoxy)butyl]naphthamide, was dissolved in 100 ml of dibutyl phthalate and 100 ml of ethyl acetate and mixed with rapid stirring with 1 kg of a 10% gelatin aqueous solution to obtain an emulsion, 350 g of which was mixed with 1 kg of a red-sensitive silver iodobromide emulsion (containing 50 g of silver and 60 g of gelatin, iodine content 6 mol%) and coated on the base to give a dry thickness of 3μ.

Second Layer: Intermediate Layer 100 g of the emulsion obtained by the same procedures for the first layer emulsion except that 2,5-di-t-amylhydroquinone was employed instead of the cyan coupler was mixed with 1 kg of a gelatin and coated thereon at a dry thickness of 1μ.

Third Layer: Green-Sensitive Emulsion Layer 100 g of a magenta coupler, 1-(2,4,6-trichlorophenyl)-3-[3-(2,4-di-t-amylphenoxyacetamido)benzamido]-5-pyrazolone, was dissolved in 100 ml of tricresyl phosphate and 100 ml of ethyl acetate and mixed with rapid stirring with 1 kg of a 10% gelatin aqueous solution to obtain an emulsion, 560 g of which was mixed with 1 kg of a green-sensitive silver iodobromide emulsion (containing 50 g of silver and 60 g of gelatin, iodine content 7 mol%) and coated at a dry thickness of 4.5μ.

Fourth Layer: Yellow Filter Layer

An emulsion containing a yellow colloidal silver was coated at a dry thickness of 1μ.

Fifth Layer: Blue-Sensitive Emulsion Layer 940 g of the emulsion obtained by the same procedures for the first layer emulsion, except that the cyan coupler was replaced by a yellow coupler, viz., Coupler (6) of this invention, was mixed with 1 kg of a blue-sensitive silver iodobromide emulsion (containing 60 g of silver and 60 g of gelatin, iodine content 5 mol%) and coated at a dry thickness of 3.5μ.

Sixth Layer: Protective Layer

A 5% gelatin aqueous solution was coated at a dry thickness of 1μ.

The multilayered coated film thus-obtained was designated Sample K.

Instead of the emulsion in the fifth layer above, emulsions containing Couplers (3), (17) and (1) as the yellow coupler, a coupler (V) described in British Pat. No. 1,450,479 and a coupler (VI) described in British Pat. No. 1,476,760 both as the comparative couplers, respectively, were used. By the similar procedures to those for Sample K, there were obtained Samples L, M, N, O and P, respectively.

Each of these films was exposed to light for sensitometry and subjected to the same color reversal process steps as Example 3.

Each of the samples thus obtained was measured for optical density using a blue light filter, a green light filter and a red light filter.

The chemical structures of the comparative couplers (V) and (VI) are as follows:

Coupler (V)

-continued

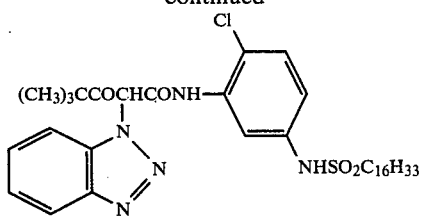

Coupler (VI)

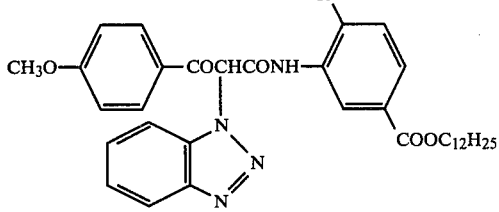

The gamma values and the maximum densities of the respective yellow color images obtained from these samples are summarized in Table 4 below.

TABLE 4

Comparison in Performance between Samples K, L, M, N, O & P

| Sample | Coupler Used | Gamma | Maximum Density |
|---|---|---|---|
| K (invention) | (6) | 1.90 | 3.27 |
| L (invention) | (3) | 2.01 | 3.40 |
| M (invention) | (17) | 1.95 | 3.25 |
| N (invention) | (1) | 1.94 | 3.20 |
| O (comparative) | (V) | 1.12 | 2.10 |
| P (comparative) | (VI) | 1.46 | 2.45 |

From Table 4 above, it can be seen that the coupler in accordance with the invention has a higher maximum density and gamma as compared with the comparative couplers.

While the invention has been described in detail and with reference to specific embodiments thereof, it will be apparent to one skilled in the art that various changes and modifications can be made therein without departing from the spirit and scope thereof.

What is claimed is:

1. A silver halide color photosensitive material comprising a yellow-dye-forming coupler having the formula (I):

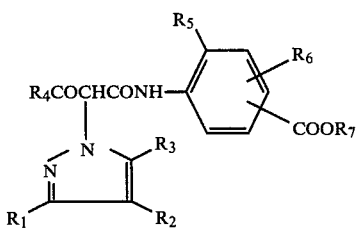

wherein $R_1$, $R_2$ and $R_3$ each independently represents a hydrogen, a halogen, an alkyl group, an alkoxy group, an aryloxy group, an alkoxycarbonyl group, an aryl group, a heterocyclic group or a carboxyl group; $R_4$ represents an aryl group or a tertiary alkyl group; $R_5$ and $R_6$ each independently represents a hydrogen, a halogen or an alkoxy group; and $R_7$ represents a substituted or unsubstituted alkyl group.

2. A silver halide color photosensitive material as in claim 1, wherein $R_4$ represents an aryl group substituted with an alkyl group, an acylamino group or an alkoxy group.

3. A silver halide color photosensitive material as in claim 1, wherein $R_1$ is selected from the group consisting of hydrogen, methyl and ethylcarboxylate.

4. A silver halide color photosensitive material as in claim 1, wherein $R_2$ is selected from the group consisting of hydrogen, chlorine, bromine, phenyl, methyl, t-butyl, toluoyl, methoxy, carboxy, and n-hexadecyl.

5. A silver halide color photosensitive material as in claim 1, wherein $R_3$ is selected from the group consisting of hydrogen, methyl, and ethylcarboxylate.

6. A silver halide color photosensitive material as in claim 1, wherein $R_4$ is selected from the group consisting of

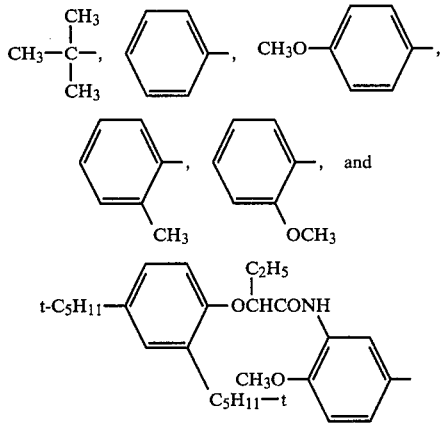

7. A silver halide color photosensitive material as in claim 1, wherein $R_5$ is selected from the group consisting of hydrogen, chlorine, methoxy and tetradecyloxy group.

8. A silver halide color photosensitive material as in claim 1, wherein $R_7$ is selected from the group consisting of

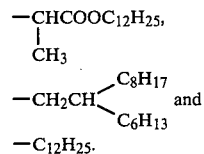

9. A silver halide color photosensitive material as in claim 1, wherein the coupler is used in an amount from about 5 to 1,500 g per mol of silver halide in association therewith.

10. A silver halide color photosensitive material as in claim 1, wherein the coupler is used in an amount of from 10 to 500 g per mol of silver halide in association therewith.

11. A silver halide color photosensitive material as in claim 1, wherein said photosensitive material is a color reversal film.

12. A silver halide color photosensitive material as in claim 1, wherein said photosensitive material is a color paper.

* * * * *